(12) United States Patent
Chen et al.

(10) Patent No.: US 7,822,557 B2
(45) Date of Patent: Oct. 26, 2010

(54) ANALYTE SENSORS AND METHODS

(75) Inventors: Ting Chen, Cedar Park, TX (US); Benjamin J. Feldman, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 831 days.

(21) Appl. No.: 11/555,167

(22) Filed: Oct. 31, 2006

(65) Prior Publication Data

US 2008/0102441 A1    May 1, 2008

(51) Int. Cl.
*G01N 27/406*    (2006.01)
*G01N 31/00*    (2006.01)

(52) U.S. Cl. .......................... 702/23; 702/19; 205/792; 204/403.03

(58) Field of Classification Search ........................ None
See application file for complete search history.

(56) References Cited

U.S. PATENT DOCUMENTS

| 5,620,466 | A | * | 4/1997 | Haefner et al. ................. 607/5 |
|---|---|---|---|---|
| 5,824,936 | A | * | 10/1998 | DuPuis et al. ................. 84/663 |
| 6,120,676 | A | | 9/2000 | Heller et al. |
| 6,338,790 | B1 | | 1/2002 | Feldman et al. |
| 6,444,115 | B1 | | 9/2002 | Hodges et al. |
| 6,579,690 | B1 | | 6/2003 | Bonnecaze et al. |
| 2002/0053523 | A1 | | 5/2002 | Liamos et al. |
| 2002/0148739 | A2 | * | 10/2002 | Liamos et al. .............. 205/787 |
| 2004/0079652 | A1 | | 4/2004 | Vreeke et al. |
| 2006/0169599 | A1 | * | 8/2006 | Feldman et al. ............. 205/792 |

OTHER PUBLICATIONS

Wang et al. Database Caplus DN: 96:154502. (Analytical Chemistry, 1982, 54(5), 861-964).*

* cited by examiner

*Primary Examiner*—Michael Borin
(74) *Attorney, Agent, or Firm*—Edward J. Baba; Khin K. Chin; Bozicevic, Field & Francis LLP

(57) ABSTRACT

Methods of determining analyte concentration. The methods use a fraction of the predicted total charge, from analyte electrolysis, instead of using time, for determination of a data collection endpoint. The total charge is then extrapolated from the data collection endpoint. The analyte concentration is determined from the total charge.

8 Claims, 3 Drawing Sheets

FIG. 3
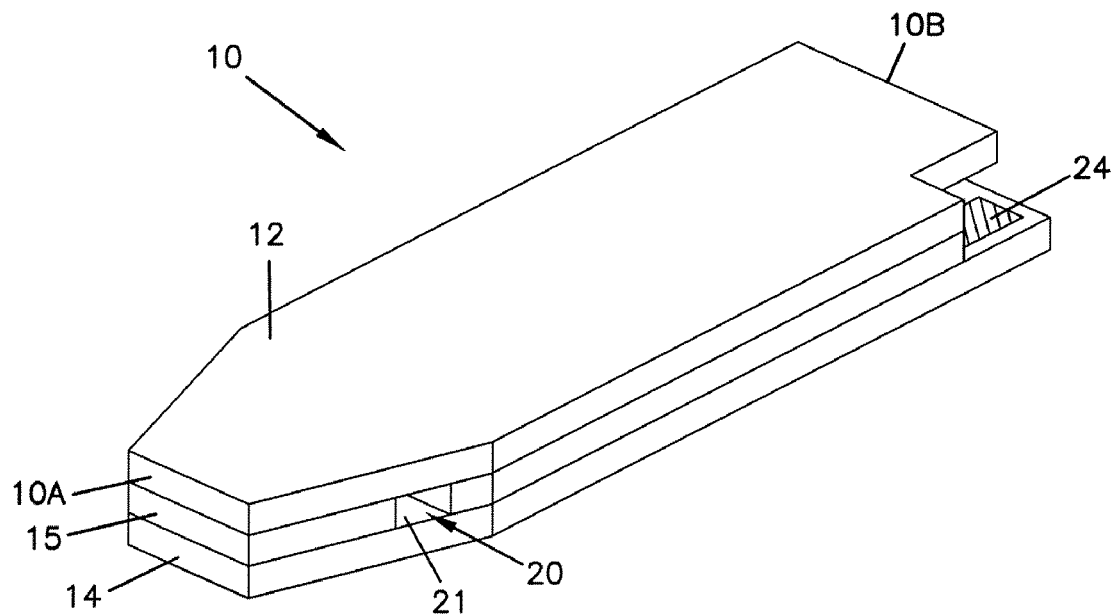
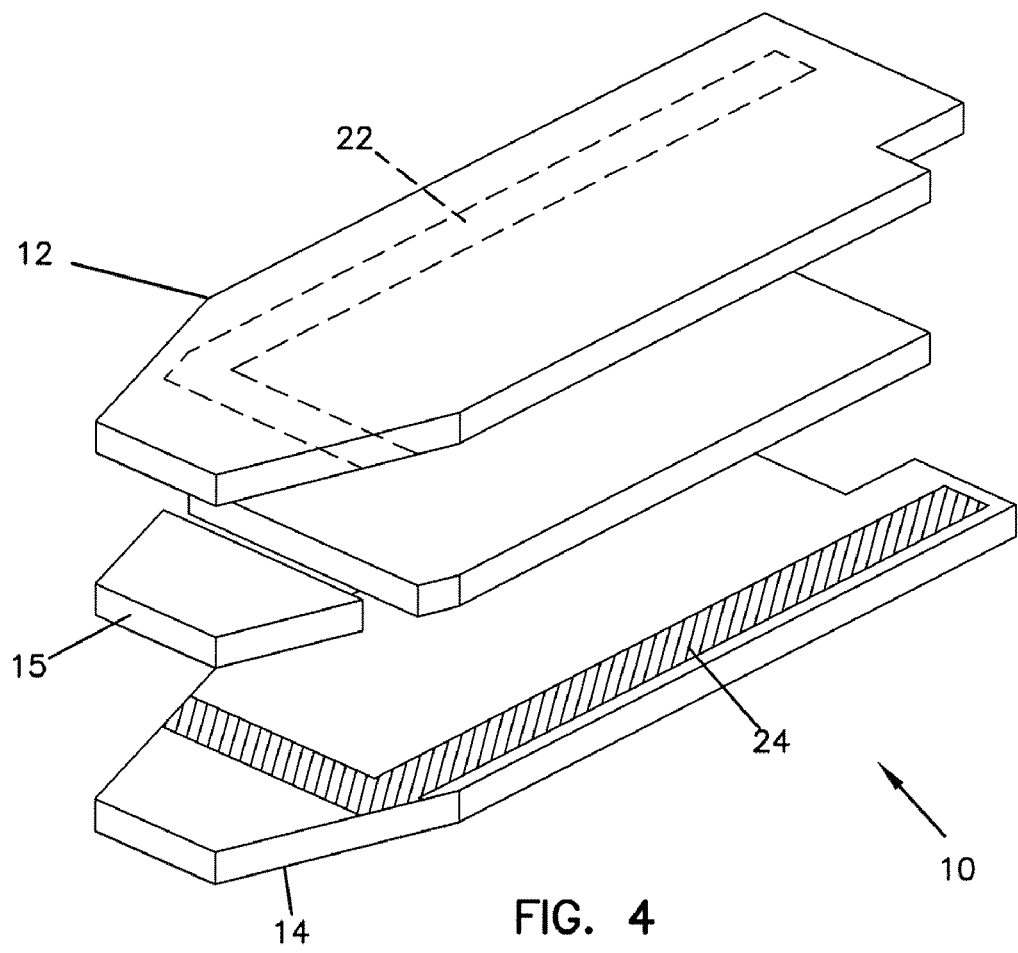
FIG. 4

ANALYTE SENSORS AND METHODS

FIELD OF THE INVENTION

This invention relates to methods for determining the concentration of an analyte in a sample, and sensors that incorporate those methods.

BACKGROUND OF THE INVENTION

Biosensors, also referred to as analytical sensors or merely sensors, are commonly used to determine the presence and concentration of a biological analyte in a sample. Such biosensors are used, for example, to detect and monitor blood glucose levels in diabetic patients.

The detection and quantification of the analyte level can be accomplished by, for example, coulometry, amperometry, potentiometry or any combination thereof. For systems using amperometry, the analyte concentration is generally determined from the average amount of the current, in amps, measured over a predetermined time period. For systems using coulometry, the analyte concentration is determined from an integrated total amount of the charge, in coulombs, measured over the period of time for required for substantial completion of sample electrolysis. The science of analyte determination is an area of ongoing development.

SUMMARY OF THE INVENTION

The present disclosure provides methods for the determination of the end-point of sample collection for analyte sensors, and sensors configured to determine an analyte concentration in a sample using those methods. The techniques of the present disclosure apply to those determination methods in which the sample, such as in an analytic device, is entirely or substantially reacted during the time frame of the analysis. An obvious electrochemical example is coulometry, and certain photometric methods are also analogous.

The techniques of the present disclosure extrapolate the total charge by continuously monitoring the measured charge and by continuously calculating the extrapolated and total charge, as well as the percent completion, as the reaction proceeds toward completion. These techniques determine a data collection endpoint based on a predetermined percentage of electrolysis of analyte, by comparing the measured charge to the total charge.

The final measured signal (e.g., for coulometry the signal is charge) is typically the sum of two components, (1) the measured signal or that signal which is actually measured prior to the data collection endpoint, and (2) the extrapolated signal, or signal calculated or otherwise expected to occur after the data collection endpoint, by the process of extrapolation. The total signal is the sum of the measured signal and the extrapolated signal.

The time of the data collection endpoint is the basis for determining the relative contributions of the measured and extrapolated signals, as well as the total signal.

In other words, the data collection endpoint is determined from a percentage of electrolysis of analyte, rather than from a predetermined time period or from the fall of the current to a predetermined percentage of the initial value.

In some embodiments, the total charge is calculated from extrapolated current decay from a data collection endpoint in real time, that endpoint having been determined from a predicted total charge. In some embodiments, the endpoint is at a predetermined percentage of the predicted total charge. The predicted total charge is used to control the current collection process until the point in time that a predetermined fraction of total analyte in the sample is electrolyzed. The method uses a fraction of the predicted total charge instead of using current or time for the determination of the data collection endpoint.

Embodiments of the present invention are used for the detection and quantification of an analyte, for example glucose, from a sample; in many embodiments the detection and quantification is accomplished with a small volume, e.g., submicroliter sample. The sensor's sample chamber may be any suitable size, including large and small volume sample chambers. In certain embodiments, such as for small volume sample chambers, the sample chamber is sized to contain no more than about 1 µL (microliter) of sample, in some embodiments no more than about 0.5 µL, in some embodiments no more than about 0.25 µL, and in other embodiments no more than about 0.1 µL of sample, where in certain embodiments the sample chamber has a volume of no more than about 0.05 µL or even about 0.03 µL or less.

Sensors of the present invention, in some embodiments, may include two substrates forming the overall sensor construction, a spacer between the substrates, at least one working electrode, at least one counter electrode, and other optional electrodes. Together, the two substrates and spacer define a sample chamber between the substrates. At least a portion of the working electrode(s) and counter electrode(s) are present in the sample chamber. The working electrode and counter electrode may be planar or facing each other.

These and various other features which characterize the invention are pointed out with particularity in the attached claims. For a better understanding of the sensors of the invention, their advantages, their use and objectives obtained by their use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views:

FIG. 3 is a schematic perspective view of a sensor suitable for use with the techniques of the present invention.

FIG. 4 is an exploded view of the sensor strip shown in FIG. 3, the layers illustrated individually.

DETAILED DESCRIPTION

Figure 1:
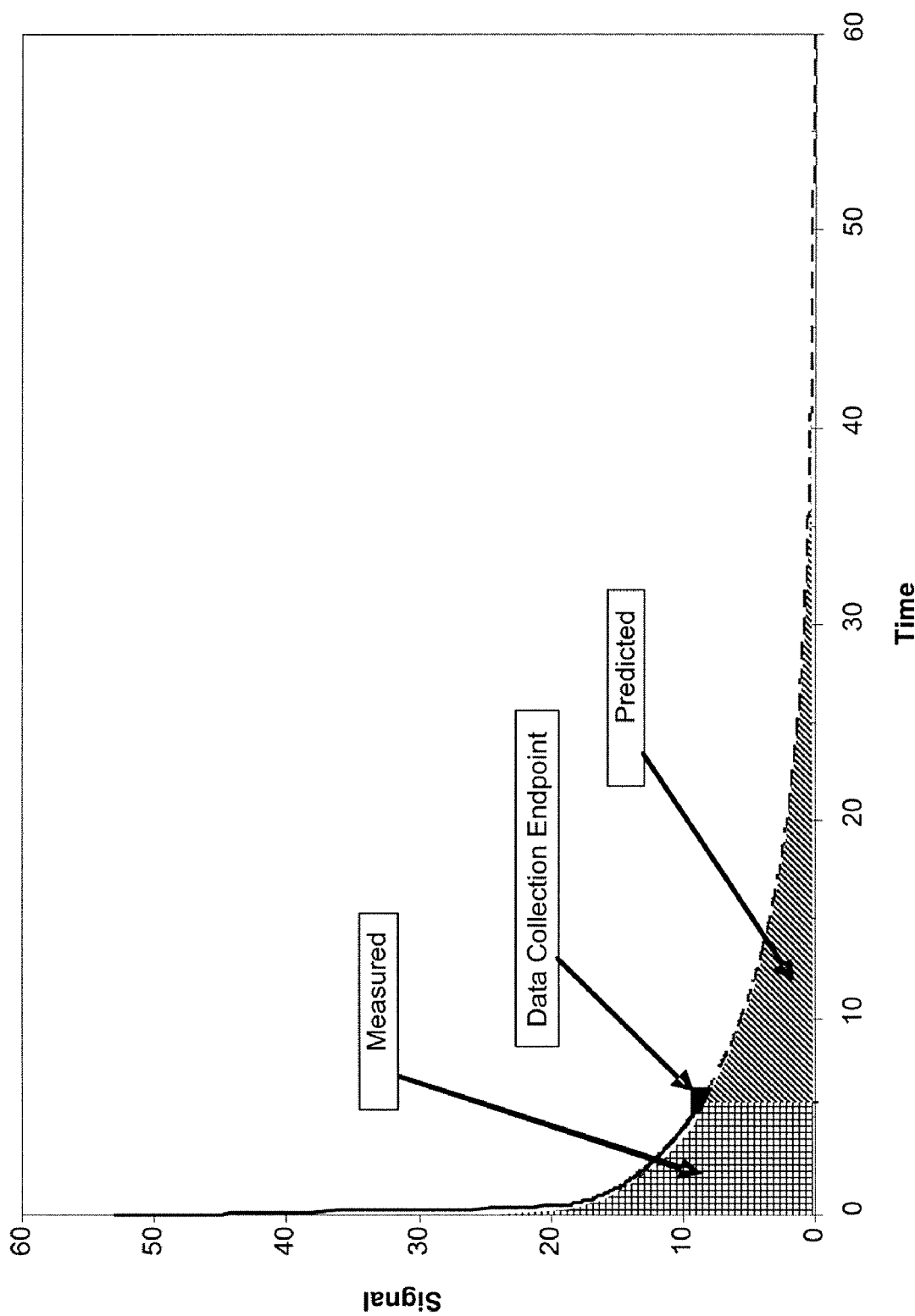
FIG. 1 is a graphical example of an analyte measurement, illustrating the general concepts of measured signal, extrapolated signal, and data collection endpoint.

As summarized above, the present disclosure is directed to methods of calculating the total charge of an electrolysis reaction, and determining an analyte concentration based on that total charge. The disclosure is also directed to sensors or biosensors that utilize a calculation for determining the analyte concentration based on a fraction of the predicted total charge. "Sensors", "electrochemical sensors", "electrochemical sensor strips", "biosensors", and variations thereof, are devices configured to detect the presence of and/or measure the concentration of an analyte in a sample via electrochemical oxidation and reduction reactions. These reactions are transduced to an electrical signal that can be correlated to an amount or concentration of analyte. A sensor may be configured as an elongated strip or otherwise.

Various electrochemical sensors, suitable for detection of analyte concentration in a sample are known. In many embodiments, in use, the sensor is connected to an electrical device, to provide a meter coupled to the sensor. The meter is configured and arranged to determine, during electrolysis of a sample in the sample chamber, the total charge, usually from a series of current values. The meter is also configured to calculate the analyte concentration in the sample based on the total charge, total estimated charge or total calculated charge from the electrolysis of the analyte.

In many embodiments, coulometry is the electroanalytical technique used for the current and/or charge determination. Although coulometry has the disadvantage of requiring the volume of the sample be known, coulometry is a preferred technique for the analysis of small samples (e.g., less than 1 microliter) because it has the advantages of, e.g., minimal temperature dependence for the measurement, minimal enzyme activity dependence for the measurement, minimal redox-mediator activity dependence for the measurement, and no error in the measurement from depletion of analyte in the sample.

Coulometry is a method for determining the amount of charge passed or projected to pass during complete or nearly complete electrolysis of the analyte. One coulometric technique involves electrolyzing the analyte on a working electrode and measuring the resulting current between the working electrode and a counter electrode at two or more times during the electrolysis. The electrolysis is complete, i.e., 100% electrolyzed, when the current reaches a value near or at zero. The charge used to electrolyze the sample is then calculated by integrating the measured currents over time and accounting for any background signal. Because the charge is directly related to the amount of analyte in the sample there is no temperature dependence of the measurement. In addition, the activity of the enzyme does not affect the value of the measurement, but only the time required to obtain the measurement (i.e., less active enzyme requires a longer time to achieve complete electrolysis of the sample) so that decay of the enzyme over time will not render the analyte concentration determination inaccurate.

Prior to the invention of this disclosure, in some designs, analyte concentration has been determined through 100% electrolysis; that is, 100% of the analyte has been electrolyzed. Using this technique, the total charge measured from the electrolysis is related to the analyte concentration abiding Faraday's Law. The total charge can be determined from measurements of the electrolysis current, it, over time, t. A series of currents ($i_x, i_{x+1}, i_{x+2}, \ldots$) is measured for a series of times ($t_x, t_{x+1}, t_{x+2}, \ldots$). The current can then be integrated over time (e.g., numerically integrated using known numerical methods) to give the total charge. The analyte concentration is then calculated from the total charge. Depending on the sensor configuration, 100% electrolysis of the analyte could take up to tens of seconds or even more.

In order to provide faster results, some designs have the current measurements end after a period of time, e.g., after a predetermined period of time, or after the current has decreased to a predetermined percentage of its initial level, when only a fraction or percentage of the analyte has been electrolyzed. The subsequent current is calculated, i.e., extrapolated, from the measured current data. The total charge is then integrated from the measured current points and the extrapolated data, and analyte concentration is calculated from the total charge.

Data extrapolation is usually based on a simplified mathematic model of the expected actual results. However, there are various factors, such as aged or deteriorated sensors, high analyte concentration, high hematocrit percentage, high sample viscosity, etc., that may cause the current decay profile to deviate from expected. As a result, there may be a significant difference in the extrapolated total charge as compared to the actual total charge. That is, the extrapolated total charge may vary substantially, depending on the time of the data collection endpoint.

The methods of this disclosure utilize values that are directly related to the percentage of analyte being electrolyzed, rather than a predetermined time period of electrolysis. In particular, the methods utilize a percentage of the total charge to select a data collection endpoint, at which extrapolation begins. In a simplified form, the methods of this disclosure predict the total charge from analyte electrolysis, take a predetermined percentage of that predicted total charge to find a data collection endpoint, and from the current at that predetermined data collection endpoint, extrapolate to determine the total charge. The extrapolated total charge is then correlated to an analyte concentration.

In accordance with methods of this disclosure, the predicted total charge is used to control the data collecting process, until a time when a predetermined fraction or percentage of analyte in the sample has been electrolyzed. The method uses a fraction or percentage of the predicted total charge for the determination of the endpoint of data collection, which is directly related to the percentage of analyte being analyzed, instead of merely using time or current, as in previous methods. From the determined data collection endpoint, the total charge is extrapolated, which is then correlated to an analyte concentration.

This calculation technique of the present disclosure is a better approach than previous extrapolation techniques, yielding more accurate concentration values and accommodating wider situations, e.g., hemocrit levels, sample temperature and/or viscosity, etc.

Methods of this disclosure use a predicted total charge to determine the data collection endpoint. This prediction of total charge is done in 'real time', during the electrolysis of the analyte. The prediction can be done by using a regular or conventional data extrapolation algorithm, which generally includes numerous iterative approximation steps, which may require the use of a powerful microprocessor in the meter. Alternately, an approximated model can be used for predicting the total charge.

A data collection endpoint is selected, based on a predetermined percentage of the electrolyzed analyte. The predetermined percentage can be any percentage greater than 0 (zero) up to 100%. In some embodiments, however, the measured percentage of total charge is at least 40%, and in other embodiments, at least 50%. That is, in some embodiments, at least 40% of the analyte has been electrolyzed at the data collection endpoint, and in other embodiments, at least 50% of the analyte has been electrolyzed. The underlying premise of the calculation technique of the present disclosure is to use a data collection endpoint that balances between the speed and accuracy of measurement, and which is directly related to the percentage of analyte being electrolyzed. From the data collection endpoint, the subsequent current is extrapolated. Various different mathematic models can be used to provide the estimation. In one embodiment, a linear extrapolation, based on the measured current data and the data collection endpoint, is used to calculate a linearly estimated current and thus a linearly estimated charge, $Q_{lin}$. In some embodiments, only of a portion of the measured current data, usually only that collected, e.g, 1 or 2 seconds prior to the data collection endpoint, is used for the linear current estimate and the linearly estimated charge. The linearly estimated charge, $Q_{lin}$, is a percentage, p, of the extrapolated portion of the charge, $Q_e$. The final $Q_e/Q_{total}$ ratio is calculated by combining with the dynamic measured portion of charge $Q_m$, as $$\frac{Q_e}{Q_{total}} = \frac{Q_e}{Q_m + Q_e} = \frac{Q_{lin}/p}{Q_m + Q_{lin}/p} \quad (1)$$

Data is collected until $Q_m = \alpha\, Q_{lin}$, where coefficient $\alpha$ controls the threshold, above which an automatic data correction by collecting more data will be applied. $\alpha$ can be optimized to balance the measurement speed and accuracy.

FIG. 1 is a graphical example of an analyte measurement, illustrating the general concepts of measured signal, extrapolated signal, and data collection endpoint.

Figure 2:
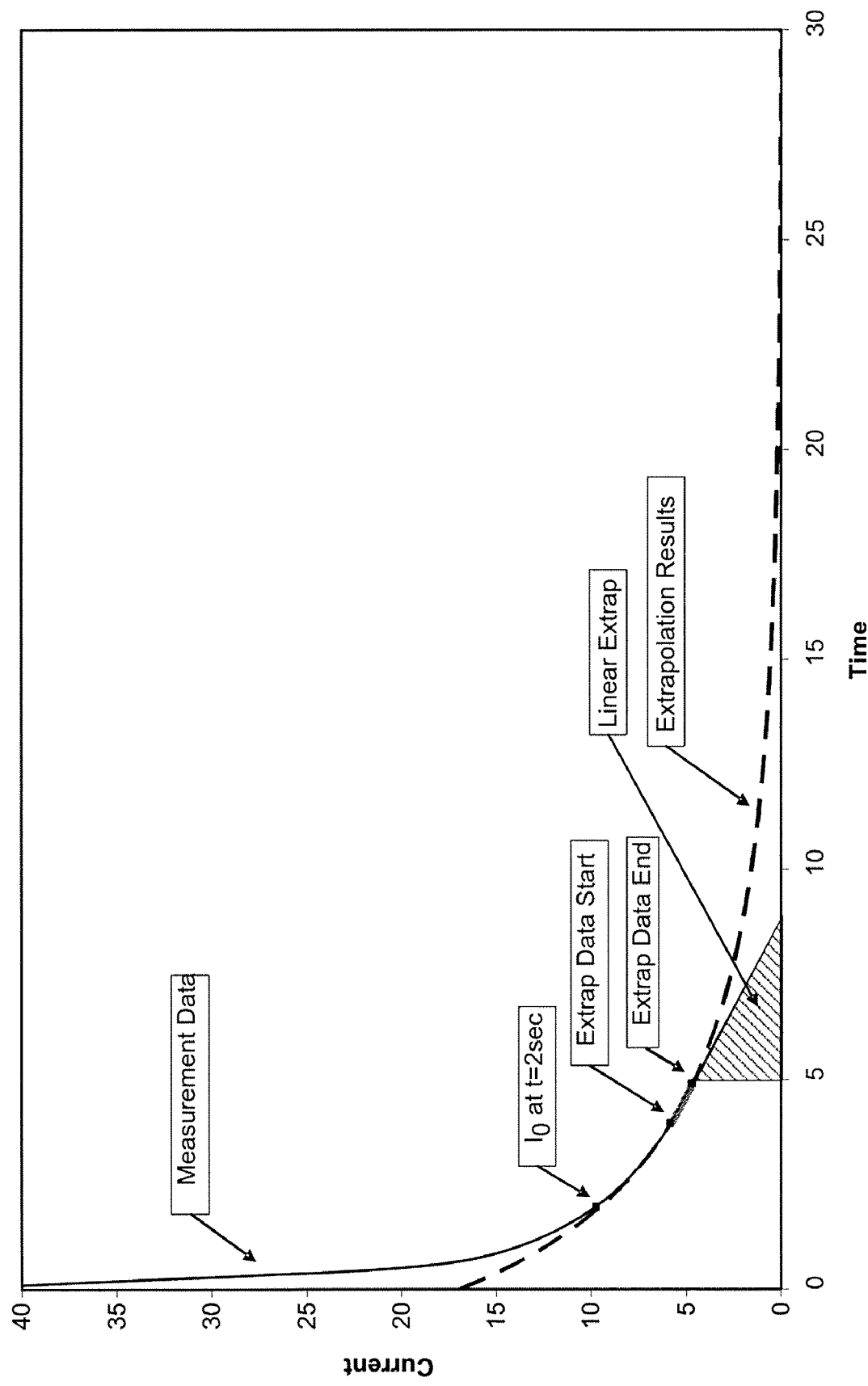
FIG. 2 is a graphical comparison of extrapolated current determined using a conventional extrapolation technique and extrapolation results using the techniques of the present disclosure.

FIG. 2 provides a graphical explanation of the methods of this disclosure using one specific example. The solid line, beginning at time 0, represents the actual current measurement. At 2 seconds, with the initial current, $I_o$, the total current is extrapolated (dashed line) and a total charge is predicted. In this example, the predetermined electrolysis percentage is set at 50% of the predicted total charge. Thus, the data collection ends at this predetermined endpoint, which in this example is approximately 5 seconds. At 5 seconds, a linear extrapolation is made. The total charge is integrated over the extrapolated linear current and the measured current data. From the total charge, the analyte concentration is determined.

In most embodiments, the predetermined endpoint for data collection is no more than about 10 seconds, in some embodiments no more than about 5 seconds, and in some embodiments, no more than about 3 seconds.

The techniques described above can be used for generally any sensor configured for use with coulometry. Referring to FIGS. 3-4, one example of an in vitro electrochemical sensor suitable for use with the invention is schematically illustrated. It is understood that the analyte measurement procedure of this disclosure could be used with any sensor configuration, and that the sensor strip illustrated in the figures is representative of only one suitable sensor.

In FIGS. 3-4, an exemplary embodiment of a sensor, suitable for use with the end-point determination methods of the present disclosure, is schematically illustrated, herein shown in the shape of a sensor strip 10. It is to be understood that the sensor may be any suitable shape. Sensor strip 10 has a first substrate 12, a second substrate 14, and a spacer 15 positioned therebetween. Together, these elements define, at least partially, a sample chamber 20 with an inlet 21 for receiving a sample to be analyzed. In some embodiments, the sample chamber is sized to contain no more than about 1 µL (microliter) of sample, in some embodiments no more than about 0.5 µL, in some embodiments no more than about 0.25 µL, and in other embodiments no more than about 0.1 µL of sample, where in certain embodiments the sample chamber has a volume of no more than about 0.05 µL or even about 0.03 µL or less.

Sample chamber 20 includes a measurement zone where the sample is electrolyzed. In some embodiments, the measurement zone is sized to contain no more than about 1 µL of sample, in some embodiments no more than about 0.5 µL, in some embodiments no more than about 0.25 µL, and in other embodiments no more than about 0.1 µL of sample, where in certain embodiments the measurement zone has a volume of no more than about 0.05 µL or even about 0.03 µL or less.

Sensor strip 10 includes at least one working electrode 22 and at least one counter electrode 24. Sensor strip 10 has a first, distal end 10A and an opposite, proximal end 10B. At distal end 10A, sample to be analyzed is applied to sensor 10. Distal end 10A could be referred as 'the fill end', 'sample receiving end', or similar. Inlet 21 is positioned at or proximate to distal end 10A. Proximal end 10B of sensor 10 is configured for operable, and usually releasable, connecting to a device such as a meter.

Sensor strip 10 is a layered construction, in certain embodiments having a generally rectangular shape, i.e., its length is longer than its width, although other shapes of sensor 10 are possible as well.

Each of the elements of sensor strip 10 is generally well known. For example, substrates 12, 14 can be inert substrates (e.g., polymeric substrates), although other substrates can be used. Electrodes 22, 24 and any other electrodes, (e.g., an indicator electrode, an insertion monitor, etc.) generally comprise a conductive material, such as carbon, silver, gold, platinum, or the like. In the illustrated embodiment, electrodes 22, 24 are facing electrodes, positioned generally opposite one another on separate substrates 12, 14. Alternate embodiments of sensors can have electrodes 22, 24 on the same substrate, e.g., as co-planar or planar electrodes.

In some embodiments, sensing chemistry material(s) are provided in sample chamber 20 to facilitate the analysis of the analyte. Sensing chemistry material facilitates the transfer of electrons between working electrode 22 and the analyte in the sample. Any sensing chemistry may be used in sensor strip 10, and the sensing chemistry may include one or more materials. The sensing chemistry generally includes an electron transfer agent that facilitates the transfer of electrons to or from the analyte. The sensing chemistry may, additionally to or alternatively to the electron transfer agent, include a redox mediator.

In use, a sample of biological fluid is provided into sample chamber 20 of sensor 10, where the level of analyte is determined using the methods described above. In many embodiments, it is the level of glucose in blood, interstitial fluid, and the like, that is determined. Also in many embodiments, the source of the biological fluid is a drop of blood drawn from a patient, e.g., after piercing the patient's skin with a lancing device or the like, which may be present in an integrated device, together with the sensor strip.

Embodiments of the subject methods include contacting the sensor with a fluid sample (obtained, e.g., from a skin incision) and transferring a volume of the fluid to the sample chamber and measurement zone of the sensor. Accordingly, bodily fluid may be first contacted with a portion of one of the substrates of the sensor prior to being contacted with the other substrate and/or sample chamber.

A common use for an analyte sensor of the present invention, such as sensor 10, is for the determination of analyte concentration in a biological fluid, such as glucose concentration in blood, interstitial fluid, and the like, in a patient or other user. Additional analytes that may be determined include but are not limited to, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Sensor strips 10 may be available at pharmacies, hospitals, clinics, from doctors, and other sources of medical devices. Multiple sensor strips 10 may be packaged together and sold as a single unit; e.g., a package of about 25, about 50, or about 100 sensors, or any other suitable number. A kit may include one or more sensors of the present invention, and additional components such as control solutions and/or lancing device and/or meter, etc.

Sensor strips 10 may be used for an electrochemical assay, or, for a photometric test. Sensor strips 10 are generally configured for use with an electrical meter, which may be connectable to various electronics. A meter may be available at generally the same locations as sensor strips 10, and sometimes may be packaged together with sensor strips 10, e.g., as a kit.

Examples of suitable electronics connectable to the meter include a data processing terminal, such as a personal computer (PC), a portable computer such as a laptop or a handheld device (e.g., personal digital assistants (PDAs)), and the like. The electronics are configured for data communication with the receiver via a wired or a wireless connection. Additionally, the electronics may further be connected to a data network (not shown) for storing, retrieving and updating data corresponding to the detected glucose level of the user.

The various devices connected to the meter may wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device has a display, such as a liquid crystal display (LCD), as well as an input device, such as buttons, a keyboard, mouse or touch-screen. With such an arrangement, the user can control the meter indirectly by interacting with the user interface(s) of the server device, which in turn interacts with the meter across a wireless link.

The server device may also communicate with another device, such as for sending data from the meter and/or the service device to a data storage or computer. For example, the service device could send and/or receive instructions (e.g., an insulin pump protocol) from a health care provider computer. Examples of such communications include a PDA synching data with a personal computer (PC), a mobile phone communicating over a cellular network with a computer at the other end, or a household appliance communicating with a computer system at a physician's office.

A lancing device or other mechanism to obtain a sample of biological fluid, e.g., blood, from the patient or user may also be available at generally the same locations as sensor strips 10 and the meter, and sometimes may be packaged together with sensor strips 10 and/or meter, e.g., as a kit.

Sensor strips 10 are particularly suited for inclusion in an integrated device, i.e., a device which has the sensor and a second element, such as a meter or a lancing device, in the device. The integrated device may be based on providing an electrochemical assay or a photometric assay. In some embodiments, sensor strips 10 may be integrated with both a meter and a lancing device. Having multiple elements together in one device reduces the number of devices needed to obtain an analyte level and facilitates the sampling process. For example, embodiments may include a housing that includes one or more of the subject strips, a skin piercing element and a processor for determining the concentration of an analyte in a sample applied to the strip. A plurality of strips 10 may be retained in a cassette in the housing interior and, upon actuation by a user, a single strip 10 may be dispensed from the cassette so that at least a portion extends out of the housing for use.

EXAMPLES

Blood samples from eight different donors were adjust to five different hematocrit levels and tested with sensors. The results from the 40% hematocrit samples from the first two donors were used to determine calibration curves of the strips which were then application to all the rest of the data.

The following table compares the results from using the sensor strips with an "old algorithm" based on end point determined by percent residue current and with the "new algorithm" which is based on a revised data collection endpoint. For the "old algorithm", the data collection endpoint was when the current reading was 50% of the peak reading. For the "new algorithm", the data collection endpoint was when 60% of the analyte had been electrolyzed. The coefficient α was 3.5.

| Glucose level | Algorithm | hematocrit | | | | |
| --- | --- | --- | --- | --- | --- | --- |
| | | 15% | 25% | 40% | 55% | 65% |
| 50 mg/dl | Old | 7.49 | 4.24 | 1.19 | 4.88 | 5.54 |
| | New | 3.17 | 0.21 | 1.56 | 2.25 | 0.40 |
| | Δ | −4.02 | −4.03 | 0.37 | −2.62 | −5.14 |
| 200 mg/dL | Old | 21.01 | 13.28 | −1.14 | −11.60 | −11.92 |
| | New | 19.80 | 12.03 | −2.14 | −7.57 | −5.77 |
| | Δ | −1.21 | −1.25 | 1.00 | −4.03 | −6.15 |
| 400 mg/dL | Old | 21.89 | 11.73 | −1.10 | −16.34 | −19.04 |
| | new | 21.79 | 11.54 | −1.24 | −11.94 | −8.17 |
| | Δ | −0.10 | −0.19 | 0.14 | −4.40 | −10.87 |

The negative signs represent a reduction in average bias, which is desirable.

The data shows that at high hematocrit levels, the algorithm improved the accuracy, however, there was minimal effect for low hematocrit samples, since the algorithm is focused on errors generated by slower reactions.

The invention has been described with reference to various specific and preferred embodiments and techniques. However, it will be apparent to one of ordinarily skill in the art that many variations and modifications may be made while remaining within the spirit and scope of the invention. For example, the invention has described primarily with respect to an electrochemical sensor strip for exemplary purposes only. It is to be understood that the sensors of the invention may be optical sensors, etc. and/or those that utilize methods such as amperometry or potentiometery.

All patents, applications and other references in this specification are indicative of the level of ordinary skill in the art to which this invention pertains. All patents, patent applications and other references are herein incorporated by reference to the same extent as if each individual patent, application or reference was specifically and individually incorporated by reference.

What is claimed:

1. A method for determining the concentration of an analyte in a sample, the method comprising:
    applying a sample to an analyte sensor, wherein the analyte sensor comprises a working electrode and a counter electrode;
    applying a current to the working electrode and counter electrode;
    measuring a predetermined amount of a current decay for the current;

predicting a first total signal value for complete reaction of the analyte from the measured current decay;

determining a data collection endpoint, wherein the data collection endpoint is a predetermined percentage of the predicted first total signal value;

measuring current decay until the data collection endpoint;

calculating a second total signal value at the data collection endpoint; and determining the concentration of the analyte based on the calculated second total signal value and the measured current decay until the data collection endpoint.

2. The method of claim 1, wherein the first total signal value is the sum of a measured signal and an extrapolated signal.

3. The method of claim 2, wherein the signal is charge and the reaction is electrolysis, and the method comprises:

predicting a total charge for complete electrolysis.

4. The method of claim 3, wherein the electrolysis comprises coulometry.

5. The method of claim 3, further comprising:

determining a predicted charge from an extrapolated linear current decay made at the data collection endpoint.

6. The method of claim 5, wherein determining the predicted charge comprises:

integrating the extrapolated linear current decay made at the data collection endpoint and the measured current decay prior to the data collection endpoint to determine the total charge.

7. The method of claim 3, wherein electrolysis comprises amperometry.

8. The method of claim 3, wherein electrolysis comprises potentiometry.

* * * * *